United States Patent [19]

Hermecz et al.

[11] Patent Number: 4,588,526
[45] Date of Patent: May 13, 1986

[54] BRONCHODILATORY AZEPINO(1,2-A)PYRIMIDINE DERIVATIVES AND ACID ADDITION SALTS THEREOF AND BRONCHODILATING PHARMACEUTICAL COMPOSITIONS CONTAINING SAME

[75] Inventors: István Hermecz; Lelle Vasvári née Debreczy; Ágnes Horváth, all of Budapest; József Kökösi, Budaörs; Sándor Virág; Tibor Breining, both of Budapest, all of Hungary

[73] Assignee: Chinoin Gyogyszer es Vegyeszeti Termekek Gyara Rt, Budapest, Hungary

[21] Appl. No.: 550,937

[22] Filed: Nov. 10, 1983

[30] Foreign Application Priority Data

Nov. 16, 1982 [HU] Hungary ............................... 3671/82

[51] Int. Cl.[4] ................... C07D 487/04; A61K 31/505
[52] U.S. Cl. .................................. 260/243.3; 544/252
[58] Field of Search ...................... 544/252; 260/243.3; 424/251; 514/250

[56] References Cited

U.S. PATENT DOCUMENTS 4,220,771  9/1980  Hermecz et al. .................. 544/252

FOREIGN PATENT DOCUMENTS 2812586  9/1978  Netherlands .
2836449  3/1979  Netherlands .

OTHER PUBLICATIONS

Szasz, Chem. Abst. vol. 100 (1984) 51009a.
Hanko Novak, Chem. Abst. vol. 100 (1984) 51010u.
Stasza, Chem. Abst. vol. 100 (1984) 51014y.
Tetsuji Kametani et al, Journal of the American Chem. Society (1977) pp. 2306–2309.
Hermecz et al., Chem. 101: 130705y (1984).
Atal, C. K., *Chemistry and Pharmacology of Vasicine A New Oxytocic and Abortifacient*, Regional Research Laboratory, Jammu, India, pp. 138–139 (1980).
Drugs of Future, 1981, 6, p. 362.

*Primary Examiner*—Mark L. Berch
*Assistant Examiner*—Cecilia Shen
*Attorney, Agent, or Firm*—Karl F. Ross; Herbert Dubno

[57] ABSTRACT

The invention relates to new azepino[1,2-a]pyrimidine derivatives—of the general formula

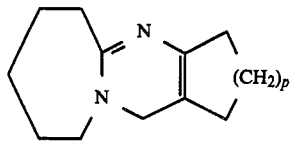

wherein p=1, 2
and acid addition salts thereof which can be prepared by
(a) reacting a compound of the formula

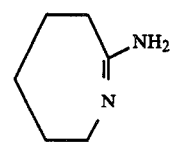

with a compound of the general formula

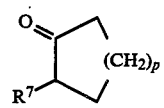

wherein p is as defined above and $R^7$ is alkoxycarbonyl containing 2 to 5 carbon atoms or carboxamido or
(b) reacting a compound of the general formula

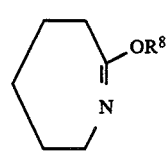

wherein $R^8$ is alkyl containing 1 to 4 carbon atoms with a compound of the general formula

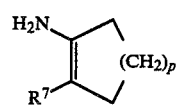

wherein $R^7$ is as defined above and if desired converting a compound of the general formula I to acid addition salt thereof or setting it free from the salt thereof.

The new compounds show bronchodilatory activity.

7 Claims, No Drawings

BRONCHODILATORY AZEPINO(1,2-A)PYRIMIDINE DERIVATIVES AND ACID ADDITION SALTS THEREOF AND BRONCHODILATING PHARMACEUTICAL COMPOSITIONS CONTAINING SAME

FIELD OF THE INVENTION

The present invention relates to new azepino[1,2-a]-pyrimidine derivatives of the formula

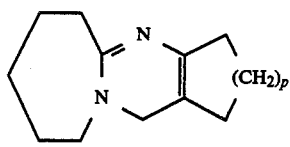

I wherein p represents 1 or 2.

BACKGROUND OF THE INVENTION

In GBP Pat. No. 2 003 870 compounds of the formula

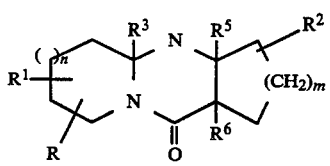

VI are disclosed
wherein
R stands for hydrogen, halogen, alkyl containing 1 to 4 carbon atoms, hydroxy, nitro, amino, carboxy or a carboxylic acid derivative group,
$R^1$, $R^2$ and $R^4$ stand for hydrogen or alkyl containing 1 to 4 carbon atoms
$R^3$, $R^5$ and $R^6$ represent hydrogen or
$R^3$ and $R^4$ and/or $R^5$ and $R^6$ together form a further chemical bond,
m stands for 1, 2, 3 or 4,
stands for 0, 1, 2 or 3 and the dotted line represents an optionally present further bond.

The compounds disclosed in the above patent specification show CNS activity, particularly analgesic activity.

We have now found that the new compounds according to the invention—not disclosed specifically in the above British patent specification—show an outstanding bronchodilatory activity without possessing CNS activity.

It is also known that 6,7,8,9,10,12-hexahydroazepino[2,1-b]quinazoline-12-one of the formula

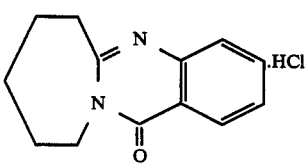

VII displays bronchodilatory activity (Drugs of the Future 1981, 6, 362).

DESCRIPTION OF THE INVENTION

We have found that the bronchodilatory activity of the compounds of the formula I of the invention significantly surpasses that of the known compound of the formula VII and that of the commercially available theophilline-anisate of similar field of activity.

The activity of the compounds of the invention was examined by Konzett test (Konzett H. and, Rossler R., Arch. Exp. Path. Pharm., 1940, 195 71) using guinea-pigs. The activity was determined on the basis of inhibition of spasm induced by three endogenic spasmogenic agents (5-hydroxy-tryptamine histamine, acetylocholine). The results are summarized in Table 1.

TABLE 1

| Test-compound | $ID_{50}$/μmole/kg spasm inhibition induced by | | |
|---|---|---|---|
| | 5-hydroxy-tryptamine | histamine | acetylcholine |
| VIII | 3.0[x] | 3.1[x] | 7.8[x] |
| IX | 15.7 | 5.4 | 6.3 |
| X | 13.8 | 6.5 | 3.7 |
| VII (known) | 36.0 | 6.2 | 26.3 |
| theophilline anisate (known) | 14.0 | 14.0 | 22.0 |

[x]long-lasting activity

As a further Example the activity of the compound of the formula IX is illustrated by human bronchus test. Human bronchus obtained surgically was dipped into an oxygenized physiological solution of 37 C. The contraction is induced by 1 μmole Carbacol. The amount of the active ingredient necessary for 50% inhibition is determined. The results are summarized in Table 2.

TABLE 2

Determination of bronchilatory activity on human bronchus

| Compound | Dosage mole/l | spasm reduction % | IC$_{50}$ mole/l |
|---|---|---|---|
| IX | 10$^{-6.0}$ | 3 | |
| | 10$^{-5.5}$ | 23 | |
| | 10$^{-5.0}$ | 48 | 5.4 |
| | 10$^{-4.5}$ | 113 | |
| | 10$^{-4}$ | 184 | |
| theophilline anisate | 10$^{-4.5}$ | 5 | |
| | 10$^{-4.25}$ | 10 | 150.0 |
| | 10$^{-4.0}$ | 28 | |
| | 10$^{-3.75}$ | 64 | |

The compounds of the formula

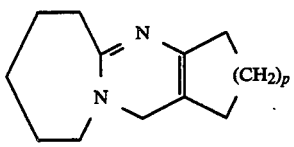   I wherein p stands for 1 or 2
and acid addition salts thereof can be prepared by
(a) reacting a compound of the formula

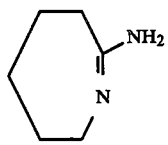   II with a compound of the formula

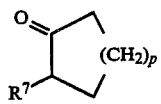   III wherein p is as defined above and R$^7$ stands for alkoxy carbonyl of 2 to 5 carbon atoms or carboxamido—or
(b) reacting a compound of the formula

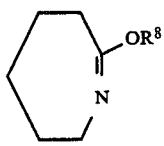   IV wherein R$^8$ represents alkyl having 1 to 4 carbon atoms with a compound of the formula

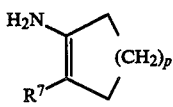   V wherein R$^7$ is as given above and converting, if desired, the obtained compound of the formula I to an acid addition salt or setting it free from the salt thereof.

The reaction of the compound of the formula II with the compound of the formula III—wherein p is given above and R$^7$ is alkoxycarbonyl of 2 to 5 carbon atoms or carboxamido—or the reaction of the compound of the formula IV—wherein R$^8$ is alkyl containing 1 to 4 carbon atoms—with a compound of the formula V—wherein R$^7$ is as defined above—are preferably conducted in an inert solvent under heating. As inert solvents alcohols, preferably methanol, ethanol, etc., aromatic hydrocarbons, such as benzene, toluene xylene, halogenated hydrocarbons, such as chloroform, dichloromethane, chlorobenzene, carbon tetrachloride, or ketones, preferably acetone, methyl ethylketone, esters, preferably ethyl acetate may be used.

The reaction is preferably carried out at the boiling point of the inert solvent. The residue obtained after the evaporation of the reaction mixture is crystallized from a suitable solvent or solvent mixture.

Acid addition salts may be formed from the compounds of the formula I by methods known per se using pharmaceutically acceptable inorganic or organic acids. Hydrogen halides, such as hydrobromide, hydrochloride, hydroiodide and salts of sulfuric acid, phosphoric acid, perchloric acid, formic acid, acetic acid, citric acid, maleic acid, fumaric acid etc. may be prepared.

The compounds of the formulae II, III, IV and V used as starting materials are commercially available compounds or can be prepared from the commercially available derivatives thereof by methods known per se (J. Am. Chem. Soc. 1948, 70, 21115, Zsur. Prikl. Him. 1965, 38, 1097, J. Pharm. Sci. 1964, 53, 1427, FR P 1 367 799).

The compounds of the formula I and pharmaceutically acceptable salts thereof can be utilized as active bronchodilatators. The toxicity of the compounds of the formula I is low, LD$_{50}$ is above 500 mg/kg when administered per os on rats and mice.

The compounds of the formula I are used as active ingredients of pharmaceutical compositions admixed with inert solid or liquid organic or inorganic carriers. The compositions are prepared by methods known per se.

The compositions are prepared in forms suitable for administration per os, parenterally or by inhalation such as tablets, dragees, capsules, lozenges, powder mixtures, aerosol sprays, aqueous solutions or suspensions or injectable solutions or syrups. The compositions can contain solid carriers or diluents, sterile aqueous solvents or non-toxic organic solvents. To the orally administered compositions sweetening of flavoring agents may be added.

The orally used tablets may contain as carriers lactose, sodium citrate, calcium carbonate, as well as disintegrating agents, such as starch, alginic acid; lubricants, such as talc, sodium lauryl sulphate or magnesium stearate. Capsules may contain lactose or polyethylene glycol as carrier. The aqueous suspension may contain emulsifiers or suspending agents. As a diluent for organic suspensions ethanol, glycerol or chloroform may preferably be employed.

For parenteral use and inhalation the active ingredient may be dissolved or suspended in a suitable medium, such as peanut oil, sesame oil, polypropylene glycol or water. The injection compositions may be administered intravenously or subcutaneously. The injectable solutions may preferably be prepared in an aqueous medium, the pH is adjusted to a suitable value. The solutions can be, if necessary, prepared in salt or glucose solution.

The active ingredient content of the pharmaceutical compositions can be varied within wide limits and can be in the range of 0.005 to 90%.

The daily active ingredient dosage can be varied within wide limits and depends on the severity of the condition of the patient, of his age, weight and on the formulation of the medicine and on the activity of the active ingredients. For oral use the daily dosage is generally in the range of 0.05 to 15 mg/kg, for inhalation or intravenous administration the dosage is in the range of 0.0001 to 5 mg/kg in a single or divided doses. On the basis of the prescription of the physician doses outside of this range are also possible.

SPECIFIC EXAMPLES

Further details of the invention are given in the following Examples which serve only for illustration and not for limitation.

EXAMPLE 1

148 g. (1 mole) of 2-amino-4,5,6,7-tetrahydro-3H-azepine hydrochloride are dissolved in 600 ml. of ethanol and a sodium-ethoxide solution prepared of 23 g. of sodium metal and 600 ml. of ethanol is added dropwise. The solution is stirred for 1 hour and the precipitated sodium chloride is filtered off. To the solution 170 g. (1 mole) of 2-ethoxy-carbonyl-cyclohexanone are added and the reaction mixture is heated for 5 hours on a hot water bath. The ethanol is then distilled off at reduced pressure. The residual solid is suspended in acetone, filtered and washed with some acetone.

179 g. (82%) of 2,3-tetramethylene-4-oxo-4,6,7,8,9-10-hexahydro-azepino-[1,2-a]pyrimidine are obtained. M.p. 152°–153° C. Analysis for the formula $C_{13}H_{18}N_2O$ calculated: C 71.57%; H 8.32%; N 12.84%; found: C 71.52%; H 8.30%; N 12.88%.

EXAMPLE 2

20 g. of 2,3-tetramethylene-4-oxo-4,6,7,8,9,10-hexahydro-azepino[1,2-a]pyrimidine are dissolved in 200 ml. of ethyl acetate and the solution is saturated with dry hydrochloric acid gas under cooling with water. The precipitated white solid is filtered and washed with ethyl acetate, 2,3-Tetramethylene-4-oxo-4,6,7,8,9,10-hexahydroazepino[1,2-a]pyrimidine hydrochloride is obtained, yield: 20.8 g. (89%), melting point: 218° C. Analysis for the formula: $C_{13}H_{19}N_2OCl$ calculated: C61.28%; H 7.51%; N 10.99%; Cl 13.91%; found: C 61.31%; H 7.49%; N 10.95%; Cl 13.87%.

EXAMPLE 3

14.8 g. (0.1 mole) of 2-amino-4,5,6,7-tetrahydro-3H-azepine hydrochloride are dissolved in 50 ml. of ethanol and a sodium ethoxide solution prepared of 2.3 g. of sodium metal in 50 ml. ethanol is added dropwise. After 1 hour the precipitated sodium chloride is filtered off. To the solution 15.6 g. (0.1 mole) of 2-ethoxy-carbonyl-cyclopentanone are added. The reaction mixture is heated for 7 hours on a hot water bath. The ethanol is then distilled off at reduced pressure. The residual oily product is taken up in 80 ml. of a 5% by W/V aqueous hydrochloric acid solution and the aqueous layer is shaken out twice with 10 ml. of ether. The aqueous layer is then neutralized with sodium hydrogen carbonate solution and extracted four times with 20 ml. of chloroform. The combined chloroform layers are dried on anhydrous sodium sulphate and evaporated. The residual oily product slowly crystallizes upon standing.

4-Oxo-2,3-trimethylene-4,6,7,8,9,10-hexahydroazepino[1,2-a]pyrimidine are obtained, yield: 12.7 g. (62%), which upon recrystallization from methyl ethyl ketone melts at 96°–98° C. Analysis for the formula: $C_{12}H_{16}N_2O$ calculated: C 70.55%; H 7,89%; N 13.71%; found: C 70.59%; H 7.85%; N 13.66%.

EXAMPLE 4

10 g. of 2,3-Trimethylene-4-oxo-4,6,7,8,9,10-hexahydro-azepino[1,2-a]pyrimidine are dissolved in 50 m. of ethyl acetate and to the solution hydrochloric acid gas is introduced. The ethyl acetate solution is evaporated. The residual partly solid product is digested with a mixture of ethyl acetate and ether and thus white crystals are obtained. The crystals are filtered and washed with diethyl ether. The crystals are filtered and washed with diethyl ether, 2,3-Trimethylene-4-oxo-4,6,7,8,9,10-hexahydro-azepino[1,2-a]pyrimidine hydrochloride is obtained, yield: 8.5 g. (72%), melting point: 180°–182° C. Analysis for the formula $C_{12}H_{17}N_2OCl$ calculated: 59.87%; H 7.12%; N 11.64%; Cl 14.72%; found: C 60.07%; H 7.08%; N 11.39%; Cl 14.85%.

EXAMPLE 5

10 g. of 2,3-Trimethylene-4-oxo-4,6,7,8,9,10-hexahydro-azepino[1,2-a]pyrimidine are dissolved in 20 ml. of ethanol and to the solution 10 ml. of 70% by W/V perchloric acid are added. The solution of raised temperature is cooled to 0° C. and the precipitated crystals are filtered and washed with ethanol. 2,3-Trimethylene-4-oxo-4,6,7,8,9,10-hexahydro-azepino[1,2-a]pyrimidine perchlorate is obtained, yield: 12 g. (80.5%), which after recrystallization from ethanol melts at 206°–208° C. Analysis for the formula: $C_{12}H_{17}N_2O_5Cl$ calculated: C 47.30%; H 5.62%; N 9.19%; found: C 47.51%; H 5.54%; N 9.20%.

EXAMPLE 6

Preparation of 75 mg tablets 375 g. of 2,3-tetramethylene-4-oxo-4,6,7,8,9,10-hexahydro-azepino[1,2-a]-pyrimidine hydrochloride are homogenized with 525 g crystalline cellulose and 70 g of amylopectine. The blend is then granulated with 75 g of Eudragit lac solution, dried at 40° C., regranulated and homogenized with a powder mixture of 10 g of talc and 10 g. of magnesium stearate and tablets are prepared by a method known per se with 200 mg. active ingredient.

EXAMPLE 7

Preparation of 150 mg retard dragees 1500 g. of 2,3-tetramethylene-4-oxo-4,6,7,8,9,10-hexahydro-azepino[1,2-a]pyrimidine hydrochloride, 1500 g. of crystalline cellulose and 250 g. polyvinyl pyrrolidone powder are homogenized. The mixture is then granulated with a solution of 45 g of Eudragit lac in about 350 ml. of propanol. The granulate is dried at 50° C., regranulated and homogenized with a powder mixture of 65 g. talc and 45 g magnesium stearate and tablets are prepared in 345 mg. units by using a twice convex tool. The tablet dragee core is coated with a film or sugar coating by method known per se.

EXAMPLE 8

Preparation of 50 mg. capsules

A powder mixture of 500 g. 2,3-trimethylene-4-oxo-4,6,7,8,9,10-hexahydro-azepino[1,2-a]pyrimidine hydrochloride, 230 g. potato starch are wet with 10 g. gelatine, 60 g. distilled water and 10 g. of 2N hydrochloric acid and 120 g. of 90% by W/V ethanol solution in a suitable kneading mixing machine and dried at 40° C. after granulating on a 0.3 mm opening screen. The granulate thus obtained is granulated again on a 0.15 mm opening screen and admixed with a powder mixture of 50 g. of potato starch, 50 g. talc and 10 g. stearine. Hard gelatine capsules are obtained in a suitable filling equipment in 0.115 g. units. The ready capsules are packed as usual.

We claim:

1. A compound of the formula

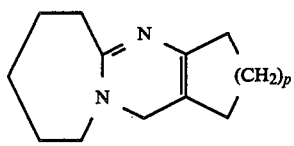

I wherein p is 1 or 2 or pharmaceutically acceptable acid addition salt thereof.

2. 2,3-Trimethylene-4-oxo-4,6,7,8,9,10-hexahydroazepino pyrimidine as defined in claim 1.

3. 2,3-Trimethylene-4-oxo-4,6,7,8,9,10-hexahydroazepino pyrimidine hydrochloride as defined in claim 1.

4. 2,3-Tetramethylene-4-oxo-4,6,7,8,9,10-hexahydroazepino pyrimidine as defined in claim 1.

5. 2,3-Tetramethylene-4-oxo-4,6,7,8,9,10-hexahydroazepino pyrimidine hydrochloride as defined in claim 1.

6. A bronchodilating composition containing as active ingredient a pharmacuetically effective amount of compound of the formula I as defined in claim 1 or a pharmaceutically acceptable acid addition salt thereof, along with a pharmaceutically acceptable inert carrier.

7. A bronchodilating method of treatment which comprises the step of administering to an animal subject in need of bronchodilation, a pharmaceutically effective amount of the compound of the Formula (I) defined in claim 1 or a pharmaceutically acceptable acid addition salt thereof.

* * * * *

UNITED STATES PATENT AND TRADEMARK OFFICE
CERTIFICATE OF CORRECTION

PATENT NO. : 4,588,526
DATED : 13 May 1986
INVENTOR(S) : Istvan HERMECZ et al

It is certified that error appears in the above-identified patent and that said Letters Patent is hereby corrected as shown below:

In the Abstract, (right column), Formula I, Column 3, line 20, and Column 7, (claim 1, line 2), the Formula I should read:

-- 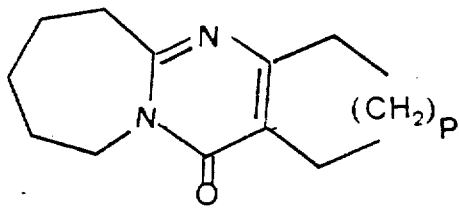 --.

Signed and Sealed this

Thirteenth Day of January, 1987

Attest:

DONALD J. QUIGG

Attesting Officer        Commissioner of Patents and Trademarks